United States Patent [19]
Lei et al.

[11] Patent Number: 5,900,485
[45] Date of Patent: May 4, 1999

[54] METHODS FOR THE MANUFACTURE OF NEOFAZODONE

[75] Inventors: Bo Lei, Thornhill; Tim Fat Tam, Woodbridge; Khashayar Karimian, Mississauga; Rudolf Kubela, Stouffville, all of Canada

[73] Assignee: Apotex, Inc., Weston, Canada

[21] Appl. No.: 08/950,768

[22] Filed: Oct. 15, 1997

[51] Int. Cl.⁶ .................. C07D 295/13; C07D 403/06
[52] U.S. Cl. ............................. 544/366; 544/393
[58] Field of Search ...................... 544/366, 393

[56] References Cited

U.S. PATENT DOCUMENTS

| | | | |
|---|---|---|---|
| 3,857,845 | 12/1974 | Palazzo | 544/366 |
| 4,338,317 | 7/1982 | Temple, Jr. et al. | 544/366 |
| 5,767,275 | 6/1998 | Nigro et al. | 544/366 |

FOREIGN PATENT DOCUMENTS

| | | |
|---|---|---|
| 1 233 826 | 3/1988 | Canada . |
| 1473000 | 5/1977 | United Kingdom . |

OTHER PUBLICATIONS

Silvestrini et al, "Pharmacological Properties of AF 1161, A New Psychotropic Drug", Int. J. Neuropharmacol. 7:587–599 (1968).

Bertoletti, P., "Valutazione dell'efficacia e della tollerabilita di un nuovo psicofarmaco nella sindrome ansioso–depres–siva (confronto in doppio cieco versus diazepam)", G. Clin. Med. 58:393 (1977).

*Primary Examiner*—Emily Bernhardt
*Attorney, Agent, or Firm*—Nixon & Vanderhye P.C.

[57] ABSTRACT

Process for the manufacture of triazolone compounds and in particular nefazodone and intermediates useful in the manufacture thereof.

17 Claims, No Drawings

METHODS FOR THE MANUFACTURE OF NEOFAZODONE

FIELD OF THE INVENTION

The invention relates to a novel process for the manufacture of triazolone compounds of Formula I which have potential antidepressant activity. A novel process to prepare nefazodone is within the scope of the present invention.

Journal of Neuropharmacology, 7 587–599 (1968) and those of etoperidone in P. Bertoletti, Clin. Med. 58,393 (1977).

Nefazodone and two processes for its preparation have) been described in Canadian Patent 1,198,436 and in PCT/EP93/03119 published May 26, 1994. The '436 patent relates to the preparation of 2-phenoxyalkyl-1,2,4 triazol-3-one derivatives Scheme 1 below depicts the two different methods described in the '436 patent.

Scheme 1

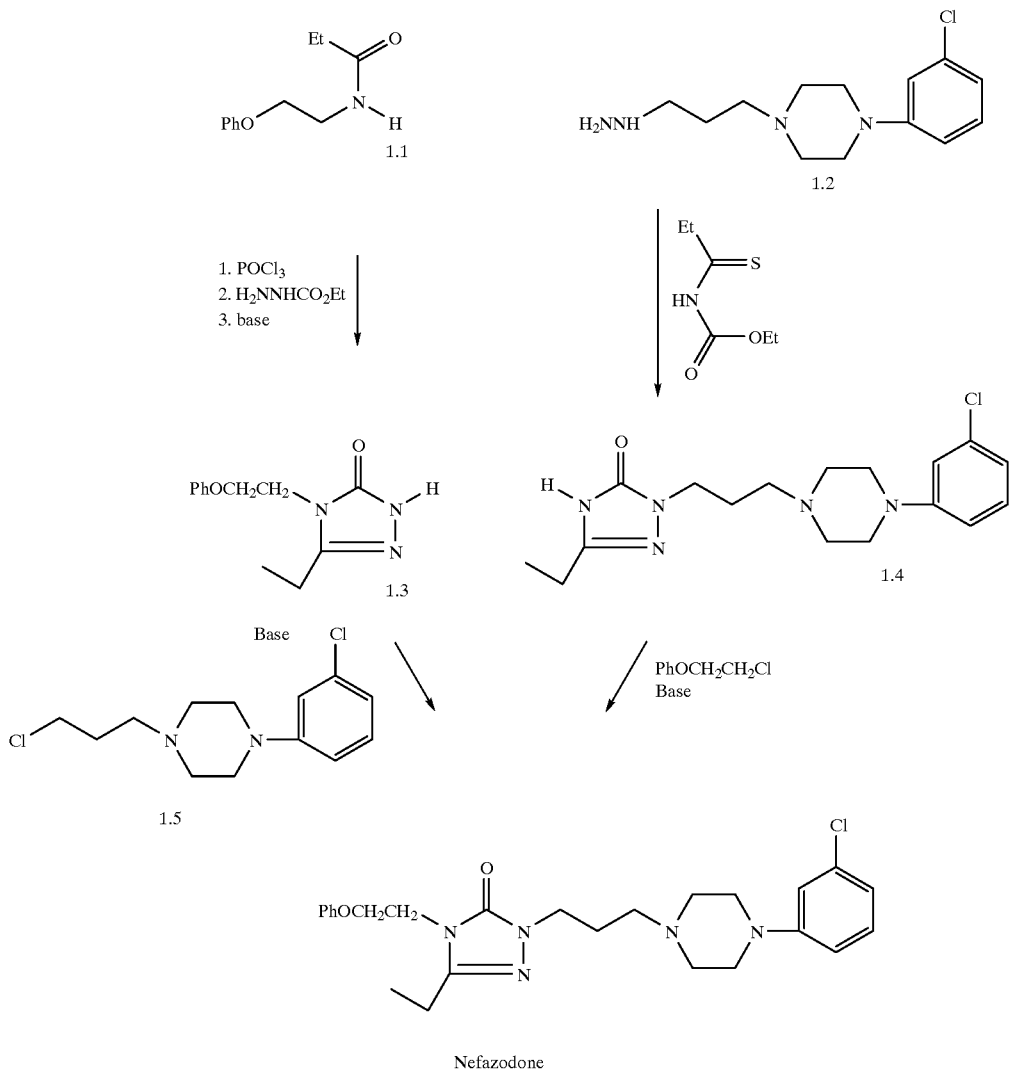

Nefazodone

BACKGROUND OF THE INVENTION 1,2,4-Triazol-3-one heterocyclic carbon compounds such as trazodone, etoperidone and nefazodone are known for their therapeutic use in treating depression. The pharmacological properties of trazodone has been published in several articles, see for example in Silvestrini, et al., International 5-Ethyl-4-(2-phenoxyethyl)-2H-1,2,4-triazol-3-one, compound 1.3 is alkylated with 1-(3-chloropropyl)-4-(3-chlorophenyl)piperazine, compound 1.5 in the presence of base to give nefazodone. Alternatively, 2-[3-[4-(3-chlorophenyl)-1-piperazinyl]propyl-5-ethyl-4H-1,2,4-triazol-3-one, compound 1.4, is alkylated with 2-phenoxyethyl chloride in the presence of base to give nefazodone.

Canadian Patent, 1,233,826 relates to an improved process for obtaining the intermediate compound of Formula 1.3 in Scheme 1. PCT/EP93/03119 teaches another process for the preparation of triazolone compounds such as nefazadone and etoperidone wherein a carbonate derivative represented as compound 2.1 in Scheme 2 below is reacted with
a N-substituted hydrazide of a carboxylic acid characterized
by Formula 2.2.

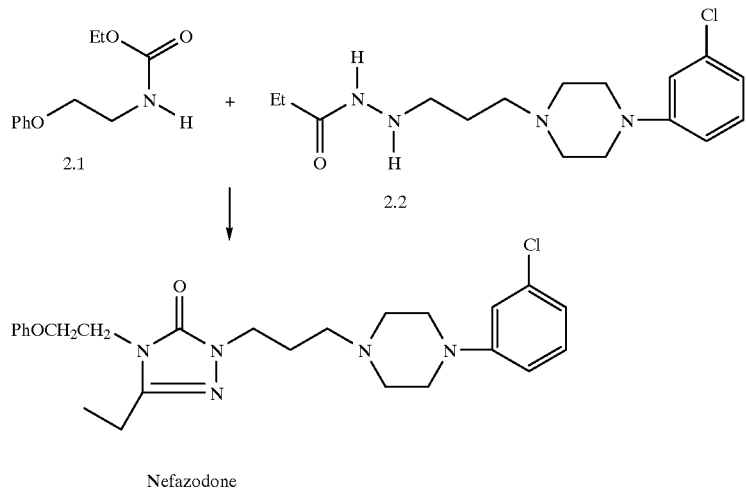

It has now been found a novel process for the preparation of triazolone derivatives and in particular for the preparation of nefazodone.

When compared to the processes of the prior art, the applicant's invention introduces a number of advantages:

First, nefazodone is produced in considerably higher yields than the process taught by the prior art.

Second, it can easily be accommodated to industrial scale production. Nefazodone is produced in four steps from commercially available starting materials.

Third, the process of the present invention introduces the substituent at the position five of 2,4-disubstituted 1,2,4-triazol-3-one at the last step of the synthesis. This synthetic pathway allows for the manufacture of various 2,4-disubstituted 1,2,4-triazol-3-one bearing a different substituent at the position five of the ring. This flexibility is extremely interesting for the synthesis of other potential antidepressant agents.

Accordingly, one object of the present invention is to provide novel process for the production of nefazodone from readily available, inexpensive and relatively safe starting material. Other objects of this invention can be recognized by those skill in the art from the summary of invention and detailed description of embodiments thereof.

SUMMARY OF THE INVENTION

One aspect of the present invention is a novel process for the manufacture of 1-[3-(4-phenyl-1-piperazinyl)propyl]-3-ethyl-4alkyl-1,2,4-triazolin-5-ones characterized by Formula and in particular for the preparation of nefazodone ($R_1$=phenoxyethyl).

(I)

wherein $R_1$ is alkyl having from 1 to 8 carbon atoms, optionally mono- or di-substituted lower alkyl wherein the alkyl group has 1 to 4 carbon atoms and the substituent is halo, aryloxy, alkoxy or aryl.

X is lower alkyl, lower alkoxy or halogen.

The term alkyl includes straight or branched chain hydrocarbon radicals having one to eight carbon atoms.

The term lower alkyl includes straight or branched chain hydrocarbon radicals having one to four carbon atoms.

The term aryl represents phenyl or naphthyl.

Halogen means chloro, bromo, iodo or fluoro.

The process comprises:
(a) reacting a compound Formula II:

(II)

wherein $R_1$ is as described above
X is as described above
with triethyl orthopropionate; or
(b) reacting an acid-addition salt of the compound of Formula II with triethyl orthopropionate.

Another aspect of this invention relates to the preparation of new intermediates characterized by Formula II useful in the preparation of triazolone compounds of Formula I.

DETAILED DESCRIPTION OF THE INVENTION

2-[3-(4-phenyl-1-piperazinyl) propyl]-4-(2-alkyl)-semicarbazide represented by Formula II is reacted with triethyl orthopropionate. The reaction is carried at temperatures between 10° C.–160° C. Alternatively the semicarbazide derivative of Formula II is converted into its acid addition salt, preferably into its methane sulfonic acid salt which is treated with triethyl orthopropionate in toluene.

Compound of Formula I is then obtained which can be converted into its hydrochloride salt in the presence of hydrochloric acid in isopropanol. If necessary the compound of Formula I is further purified by fractional recrystallization.

The semicarbazide derivatives of Formula II are prepared by reacting 1-(halophenyl)-4-(3-hydrazinopropyl) piperazine represented by Formula III:

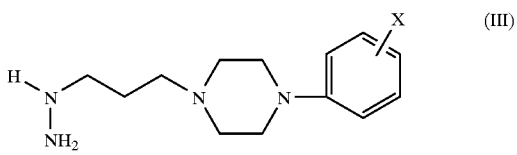

with an alkyl isocyanate of formula V.

$$R^1-N=C=O \qquad (V)$$

Compounds of Formula III are generally unstable and readily degrade to nitrogen. Their instability is the cause of numerous difficulties when attempting to scale up a process that involves such intermediates. At has now been surprisingly found that compounds of Formula III are indefinitely stable when stored on magnesium oxide. Compounds of Formula III reacts with an alkyl isocyanate of Formula V at controlled temperature, in the presence of an inert solvent. Preferably the temperature is kept between –20° C. to 20° C. The inert solvent is most preferably dichloromethane, tetrahydrofuran or toluene. The alkyl isocyanate used when nefazodone is prepared is phenoxyethyl isocyanate.

Compounds of Formula III are obtained by a process described in Examples 1(a) and 1(b) of the 1,198,436 Patent.

Example 7 of the present invention teaches the preparation of isolable forms of compounds of Formula V by modification of examples 5(a) and 5(b) of the '436 Patent.

The present invention will be more fully understood by the following examples which illustrate the invention, but are not considered limiting to the scope of the invention.

EXPERIMENTAL

EXAMPLE 1

1-(3-Chloropropyl)-4-(3-chlorophenyl)piperazine hydrochloride

A 25% NaOH solution (320 ml, 2.0 mol) is added dropwise to a stirred solution of 1-(3-chlorophenyl)-piperazine hydrochloride (196.5 g, 1.0 mol) and 1-bromo-3-chloropropane (99.0 ml, 1.0 mol) in acetone (200 ml) while maintaining temperature of 0°–10° C. After the addition is completed, the mixture is allowed to warm to room temperature and is stirred for 18 hours. The upper organic phase is then separated and concentrated under reduced pressure. The residual oil is taken up in 250 ml acetone and filtered. The filtrate is concentrated under reduced pressure and the oily residue is dissolved in 1 l of 15% boiling HCl solution. A viscous oil is separated from the cooled mixture and poured into 1 l of ice-$H_2O$ with vigorous stirring, forming white precipitates. Recrystallization of the solid from boiling water gave 171.8 g (55.6% yield) of 1-(3-Chloropropyl)-4-(3-chlorophenyl)piperazine hydrochloride; m.p 199.5–200.5° C. $^1H$ nmr (d-DMSO) δ 11.55 (bs, 1H, HCl), 7.29 (t, 1H, J=8.1 Hz, phenyl H), 7.08 (t, 1H, J=2.0 Hz, phenyl H), 6.99 (dd, 1H, J=2.1, 8.3 Hz, phenyl H), 6.89 (dd, 1H, J=1.5, 7.7 Hz, phenyl H), 3.90 (d, 2H, J=12.8 Hz, $CH_2$), 3.80 (t, 2H. J=6.4 Hz, $CH_2$), 3.58 (d, 2H, J=11.4 Hz, $CH_2$), 3.09–3.41 (overlapping 8H, $CH_2$), 2.30 (m, 2H, $CH_2$); $^{13}C$ nmr (d-DMSO) δ 150.8, 134.0, 130.7, 119.2, 115.3, 114.2, 53.3, 50.5, 44.8, 42.5, 26.2.

EXAMPLE 2

1-(3-Chlorophenyl)-4-(hydrazinopropyl)piperazine (III)

1-(3-Chloropropyl)-4-(3-chlorophenyl)piperazine hydrochloride (20.0 g, 0.065 mol) is suspended in isopropanol (65 ml) and anhydrous hydrazine (31.7 g, 0.988 mol) is added. The reaction mixture is heated at 70–80° C. for 2.5 hours and cooled to room temperature. The upper layer is separated and concentrated under reduced pressure. The residue is dissolved in isopropanol (50 ml) and the upper layer is separated, dried ($Na_2SO_4$), and concentrated to yield 16.5 g (94.5% yield) of 1-(3-chlorophenyl)-4-(3-hydrazinopropyl) piperazine (85% pure) as a viscous oil. The product is used directly without further purification or stored at room temperature in toluene or isopropanol solution by adding 1% MgO.

The hydrazine is dissolved in isopropanol and 1% magnesium oxide is added. The mixture is stirred for 30 min and filtered. The filtrate is cooled with ice-bath and one equivalent of anhydrous HCl in isopropanol is added under vigorous stirring. The precipitates are collected by filtration and dried at 60° C. under reduced pressure to afford white powder; mp 147–150° C. $^1H$ nmr (d-DMSO) δ 7.83 (bs, 3H, NH $NH_2$), 7.22 (t, 1H, J=8.1 Hz, phenyl H), 6.95 (t, 1H, J=2.0 Hz, phenyl H), 6.91 (dd, 1H, J=2.0, 8.5 Hz, phenyl H), 6.80 (dd, 1H, J=1.7, 7.8 Hz, phenyl H), 3.20 (t, 4H, J=4.5 Hz, $2CH_2$), 2.99 (t, 2H. J=7.2 Hz, $CH_2$), 2.50–2.55 (m, 4H, $2CH_2$), 2.44 (t, 2H, J=6.6 Hz, $CH_2$), 1.76–1.85 (m, 2H, $CH_2$); $^{13}C$ nmr (d-DMSO) δ 152.2, 133.8, 130.4, 118.0, 114.5, 113.6, 54.9, 52.2, 49.3, 47.5, 21.9.

EXAMPLE 3

Phenoxypropionyl chloride

Phenoxypropionic acid (249.0 g, 1.50 mol) is dissolved in four equivalents of thionyl chloride (438.0 ml, 6.0 mol) and heated to reflux until the HCl evolution has ceased. The solution is then cooled to room temperature and concentrated under reduced pressure to give 281.0 g (100% yield) of phenoxypropionyl chloride as a brown oil which solidifies on cooling. IR (KBr) $cm^{-1}$: 1793 (C=O); $^1H$ nmr ($CDCl_3$) δ: 7.31 (m, 2H, phenyl-H), 7.01 (t, 1H, J=7.5 Hz, phenyl-H), 6.92 (m, 2H, phenyl-H), 4.29 (t, 2H. J=5.9 Hz, $OCH_2$), 3.36 (t, 2H, J=5.9 Hz, $COCH_2$); $^{13}C$ nmr ($CDCl_3$) δ: 171.9, 158.0, 129.6(2C), 121.6, 114.7(2C), 62.6, 46.7.

EXAMPLE 4

Phenoxypropionyl azide

Phenoxypropionyl chloride (9.23 g, 0.05 mol) is dissolved in 100 ml acetone and cooled with an ice bath as sodium azide (3.6 g, 0.055 mol) in 10 ml water is added dropwise. After addition is completed, the reaction mixture is warmed to room temperature and stirred for 30 minutes. The solution is decanted and concentrated. The residue is dissolved in 100 ml ether and washed with saturated sodium bicarbonate and brine. The organic phase is separated, dried ($MgSO_4$) and concentrated to give 6.52 g (68.0% yield) of phenoxypropionyl azide as a yellow oil which solidifies on cooling. IR (KBr) cm$^{-1}$: 2137 (N$_3$), 1718 (C=O); $^1$H nmr (CDCl$_3$) δ: 7.31 (m, 2H, phenyl H), 6.98 (t, 1H, J=7.5 Hz, phenyl H), 6.92 (m, 2H, phenyl H), 4.26 (t, 3H, J=6.3 Hz, CH$_2$ O), 2.84 (t, 3H, J=6.3 Hz, CH$_2$ C=O); $^{13}$C nmr (CDCl$_3$) δ: 178.0, 159.0, 129.5(2C), 121.2, 114.7(2C), 62.9, 36.9.

EXAMPLE 5

Ethyl phenoxypropionate

Phenoxypropionic acid (6.64 g, 0.04 mol) is mixed with excess ethanol (10 ml) and concentrated sulfuric acid (0.5 ml) is added. The reaction mixture is refluxed for 3 hours, cooled to room temperature and concentrated. The residue is washed with 1N NaOH and brine, dried (Na$_2$SO$_4$), and concentrated to yield 7.32 g (94.3% yield) of the ester which can be used directly for the subsequent reaction without further purification. $^1$H nmr (CDCl$_3$) δ: 7.22–7.29 (overlap 2H, phenyl H), 6.88–6.966 (overlap 3H, phenyl H), 4.10–4.20 (overlap 4H, 2CH$_2$O), 2.73 (t, 2H. J=6.4 Hz, CH$_2$), 1.23 (t, 3H, J=7.1 Hz, CH$_3$); $^{13}$C nmr (CDCl$_3$) δ: 170.7, 158.7, 129.4(2C), 120.9 114.6(2C), 63.4, 60.5, 34.5, 14.1.

EXAMPLE 6

Phenoxypropionyl hydrazide

Ethyl phenoxypropionate (161 g, 0.83 mol) is cooled with an ice bath and anhydrous hydrazine (32 ml, 1 mol) is added dropwise. After the addition is completed, the solution is warmed to room temperature and stirred for 4 hours. The solution is then cooled with an ice bath under vigorous stirring. After the white precipitate formed the mixture is kept in refrigerator for 14 hours. The solid is collected by filtration, washed with cold 10% ethanol/hexane and dried in reduced pressure at 50° C. for 12 hours to give 134.7 g (90%) of phenoxypropionyl hydrazide as white powder. Mp 66–70° C.; IR (KBr) cm$^{-1}$: 3424 (NH), 1639 (C=O); $^1$H nmr (CDCl$_3$) δ: 7.45 (bs, 1H, NH), 7.25–7.32 (overlap2H, phenyl H), 6.88–7.00 (overlap 3H, phenyl H), 4.25 (t, 2H, J=5.9 Hz, CH$_2$O), 3.96 (bs, 2H, NH$_2$), 2.65 (t, 2H. J=5.9 Hz, CH$_2$); $^{13}$C nmr (CDCl$_3$) δ: 171.4, 158.1, 129.6 (2C), 121.3, 114.6 (2C), 63.7, 34.8.

The hydrochloride salt of phenoxypropionyl hydrazide is prepared by dissolving the hydrazide in dichloromethane, cooling with an ice bath and bubbling through anhydrous HCl gas until pH 3. The solid is collected by filtration, washed with cold dichloromethane and air-dried to give the hydrochloride salt as fine white powder, mp 172–174° C.

EXAMPLE 7

Phenoxyethyl isocyanate (V)

Method A: Phenoxypropionyl azide (15.2 g, 0.08 mol) is dissolved in 50 ml toluene and heated with an external oil bath. At 75–80° C. (internal temperature) vigorous N$_2$ evolution is observed and the reaction is very exothermic. The solution is refluxed for further 30 min after the gas evolution has finished. The solution is concentrated and the residue is distilled in vacuo to give 7.8 g (60% yield) of phenoxyethyl isocyanate as a colorless oil (94–96° C., 1 mmHg). IR (neat) cm$^{-1}$: 2263 (N=C=O); $^1$H nmr (CDCl$_3$) δ: 7.35 (t, 2H, J=7.8 Hz, phenyl H), 7.04 (t, 1H, J=7.3 Hz, phenyl H), 6.98 (d, 2H, J=8.3 Hz, phenyl H), 4.12 (t, 3H, J=4.2 Hz, CH$_2$O), 3.64 (t, 3H, J=4.2 Hz, CH$_2$ C=O); $^{13}$C nmr (CDCl$_3$) δ: 158.2, 129.6(2C), 121.6, 114.8(2C), 67.1, 42.7.

Method B: Phenoxypropionyl hydrazide (125.9 g, 0.7 mol) is suspended in 650 ml ice-water and concentrated hydrochloric acid (123 ml, 1.47 mol) was added. The mixture is stirred for 20 min and toluene (350 ml) is added. A solution of sodium nitrite (53.1 g, 0.77 mol) in 200 ml water is added over a period 15 min. The internal temperature is kept below 15° C. and if necessary, ice is directly added to the reaction mixture. After the addition is completed the mixture is stirred for a further 1 hour and filtered through Celite. The solid is washed with 30 ml toluene and the filtrate is separated. The aqueous layer is extracted with 200 ml toluene and the combined toluene solutions are dried over MgSO$_4$. The dried toluene solution is filtered and added dropwise to a preheated flask at 95–100° C. Nitrogen evolution occurs as the solution is dropped in. After the addition is complete, the reaction mixture is heated to gentle reflux until nitrogen evolution has ceased. The reaction mixture is cooled to room temperature and can be used directly in subsequent reactions. 1 ml of the reaction mixture is withdrawn and evaporated to dryness, and the weight of the residue is measured. This provides an estimate of the concentration of isocyanate per ml of reaction mixture.

EXAMPLE 8

2-[3-(4-[3-Chlorophenyl]-1-piperazinyl)propyl]-4-(2-phenoxyethyl)-semicarbazide (II)

A solution of phenoxyethyl isocyanate (89 g, 0.55 mol) in toluene (450 ml) is generated in situ (see example 7) and cooled to −20° C. To the solution is added a solution of 1-(3-chlorophenyl)-4-(3-hydrazinopropyl)piperazine (131.2 g, 0.49 mol) in 100 ml toluene at the speed that the internal temperature is below −10° C. After the addition is completed the mixture is stirred for 30 min at −20° C. and for 1.5 hours at 0° C. and quenched with 150 ml 1N NaOH solution. The mixture is stirred at 0° C. for 10 min and filtered through celite. The filtrate is saturated with NaCl and separated. The aqueous layer is extracted with 100 ml toluene and the combined toluene solution was dried over Na$_2$SO$_4$, filtered and concentrated to give a viscous oil. A small amount sample was purified by column chromatography (5% MeOH/CH$_2$Cl$_2$) to give a colorless oil, IR (neat) cm$^{-1}$: 3450 (NH), 1647 (C=O); $^1$H nmr (CDCl$_3$) δ: 7.24–7.29 (m, 2H, phenyl H), 7.12 (t, 1H, J=8.0 Hz, phenyl H), 6.77–6.96 (overlap 6H, phenyl H, NH), 6.69 (dd, 1H, J=2.0, 9.7 Hz, phenyl H), 4.11 (bs, 2H, NH$_2$), 4.01 (t, 2H, J=4.9 Hz, CH$_2$), 3.53–3.63 (overlap 4H, 2CH$_2$), 3.12 (t, 4H, J=4.8 Hz, 2CH$_2$), 2.53 (t, 4H, J=4.8 Hz, 2CH$_2$), 2.41 (t, 2H, J=6.5 Hz, CH$_2$), 1.75–1.84 (m, 2H, CH$_2$); $^{13}$C nmr (CDCl$_3$) δ: 159.3, 152.2, 134.9, 130.0, 129.5 (2C), 120.9, 119.2, 115.6, 114.5 (2C), 112.8, 67.7, 56.2, 52.9 (2C), 49.5, 48.5 (2C), 39.8, 24.6.

The crude product is dissolved in isopropanol, cooled with Ice bath, and two equivalents of HCl/isopropanol are added. The precipitates are collected by filtration and further purified by recrystallization from ethanol to give 170.6 g (69%) of hydrochloride salt as white crystal. Mp 172–176° C.; IR (KBr) cm-1: 3356 (NH), 1659 (C=O); $^1$H nmr (DMSO-d$_6$) δ: 10.4 (bs, 2H, NH$_2$), 8.00 (bs, 1H, NH), 7.25–7.33 (m, 3H, phenyl H), 6.87–7.04 (m, 6H, phenyl H), 4.08 (t, 2H, J=5.8 Hz, CH$_2$), 3.82–3.85 (m, 4H, 2CH$_2$), 3.51 (bs, 4H, 2CH$_2$), 3.10–3.35 (overlapping 6H, 3CH$_2$), 2.11–2.24 (m, 2H, CH$_2$); $^{13}$C nmr (DMSO-d$_6$) δ: 158.4, 157.1, 150.8, 134.0, 130.7, 129.6(2C), 120.7, 119.2, 115.3, 114.6 (2C), 114.2, 66.1, 52.7, 50.5(2C), 46.3, 44.7(2C), 39.6, 20.9; MS for free base: C$_{22}$H$_{31}$ClN$_5$O$_2$ (M+H)$^+$ calculated 432.2166, found 432.2159.

EXAMPLE 9

2[3-[4-(3-Chlorophenyl)-1-piperazinyl]-propyl]-5-ethyl-4-(2-phenoxyethyl-2H-1,2,4-triazol-3(4H)-one monohydrochloride (Nefazodone monohydrochloride)

2-[3-(4-[3-chlorophenyl]-1-piperazinyl)propyl]-4-(2-phenoxyethyl)-semicarbazide dihydrochloride (23.3 g, 46 mmol) is suspended in 50 ml toluene and refluxing with Dean-Stark apparatus to remove water. The mixture is then cooled to room temperature and triethyl orthopropionate (50 ml, about 5 eq) is added. The suspension is refluxed again with Dean-Stark apparatus. As toluene is distilled the suspension becomes a clear solution which is refluxed for 48 hours. Distillation under reduced pressure removes unreacted trietyl orthopropionate and the resulting residue is dissolved in 50 ml isopropanol, treated with HCl to pH4, stirred at 0° C. for 1 hour and standed in refrigerator for 12 hours. The solid is collected with filtration and recrystallized from ethanol to give 10.5 g (45%) of nefazodone monohydrochloride as white powder (95% pure by HPLC). Further purification is achieved by fractional recrystalization to give the product with 99.5% purity. mp 183–185° C. IR (KBr) cm−1: 2430–2800 (NH+), 1699 (C=O), 1450–1600 (aromitic); $^1$H nmr (CDCl$_3$) δ: 12.39 (s, 1H, HCl), 7.24–7.29 (m, 2H, phenyl H), 7.21 (t, 1H, J=8.0 Hz, phenyl H), 6.91–6.96 (m, 2H, phenyl H), 6.84–6.89 (m, 3H, phenyl H), 6.75 (dd, 1H, J=2.2, 8.3 Hz, phenyl H), 4.19 (t, 2H, J=5.0 Hz, CH$_2$), 4.01 (t, 2H, J=5.0 Hz, CH$_2$), 3.86 (t, 2H, J=6.3 Hz, CH$_2$, 2.96–3.07 (m, 2H, CH$_2$), 3.54–3.70 (m, 6H, 3CH$_2$), 3.09–3.16 (m, 2H, CH$_2$), 2.70(q, 2H, J=7.5 Hz, CH$_2$ C=C), 2.32–2.42 (m, 2H, CH$_2$), 1.31 (t, 3H, J=7.5 Hz, CH$_3$); $^{13}$C nmr (DMSO-d$_6$) δ: 156.8, 152.5, 149.4, 147.2, 133.7, 129.2, 128.4(2C), 120.1, 119.5, 115.4, 113.5, 113.1(2C), 63.9, 53.4, 50.1, 44.6, 41.1, 40.0, 22.0, 17.9, 8.7; elemental analysis for C$_{25}$H$_{32}$ClN$_5$O$_2$. HCl: calculated 59.38% C, 6.58% H, 13.86% N; found 59.26% C, 7.25% H, 13.61% N.

The embodiments of the present invention in which exclusive property and right is claimed are defined as follows:

What is claimed is:

1. A process for the manufacture of compounds of Formula I:

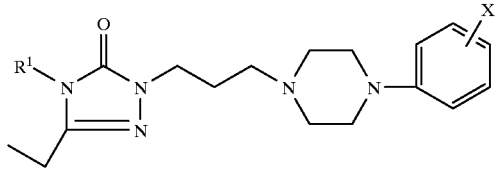

(I)

wherein R$^1$ is alkyl having from 1 to 8 carbon atoms, optionally mono- or di-substituted lower alkyl wherein the alkyl group has 1 to 4 carbon atoms and the substituent is halo, aryloxy, alkoxy or aryl X is lower alkyl, lower alkoxy or halogen which comprises:

(a) reacting a compound of Formula II:

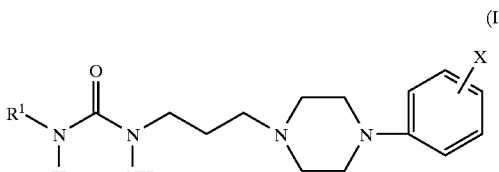

(II)

wherein R$_1$ is as described above;
X is as described above
with triethyl orthopropionate; or alternatively
(b) reacting an acid addition salt of the compound of Formula II with triethyl orthopropionate.

2. A process according to claim 1 wherein the reaction is carried out at a temperature between 10° C. and 160° C.

3. A process according to claim 1(b) wherein the acid addition salt is a sulfonic acid, and the reaction is carried out at a temperature between 10° C. and 50° C.

4. A process according to claim 3 wherein the acid addition salt is methane sulfonic acid.

5. A process according to claim 1, wherein the compound of Formula II is obtained by reacting a compound of Formula III:

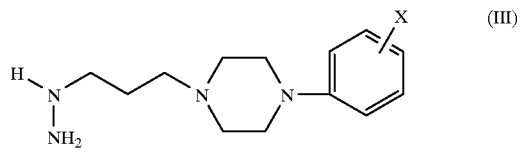

(III)

wherein X is as defined in claim 1 with a compound of Formula V:

$$R^1-N=C=O \qquad (V)$$

wherein R$^1$ is as defined in claim 1.

6. A process according to claim 5 wherein the reaction is carried out at a temperature between −20° to 20° C.

7. A process according to claim 5 wherein the reaction is carried out in the presence of an inert solvent.

8. A process according to claim 7 wherein the inert solvent is selected from the group of dichloromethane, tetrahydrofuran and toluene.

9. A process according to claim 5 wherein the compounds of Formula III are stabilized by magnesium oxide.

10. 2-[3-4[3-halophenyl]-1-piperazinyl)propyl]-4-(2-phenoxyethyl)-semicarbazide.

11. 2-[3-4[3-chlorophenyl]-1-piperazinyl)propyl]-4-(2-phenoxyethyl)-semicarbazide.

12. A compound of the formula

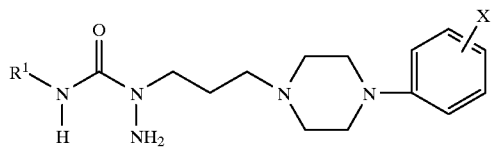

wherein R$_1$ is an alkyl of 1 to 8 carbon atoms, optionally mono- or di-substituted lower alkyl of 1–4 carbon atoms and the substituent is halo, aryloxy, alkoxy or aryl, and X is halogen.

13. A compound of the formula

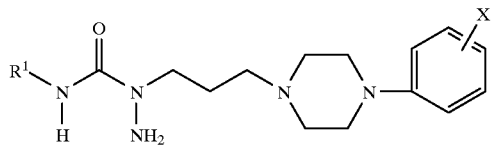

wherein R$_1$ is an alkyl of 1 to 8 carbon atoms, optionally mono- or di-substituted lower alkyl of 1–4 carbon atoms and the substituent is halo, aryloxy, alkoxy or aryl, and X is lower alkyl.

14. A compound of the formula

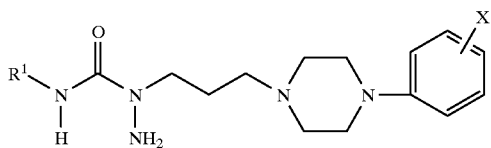

wherein $R_1$ is an alkyl of 1 to 8 carbon atoms, optionally mono- or di-substituted lower alkyl of 1–4 carbon atoms and the substituent is halo, aryloxy, alkoxy or aryl, and X is lower alkoxy.

15. A compound according to claim 12 wherein said compound is 2-[3-(4-[3-halophenyl]-1-piperazinyl)propyl]-4-(2-alkyl)-semicarbazide.

16. A compound according to claim 13 wherein said compound is 2-[3-(4-[3-alkylphenyl]-1-piperazinyl)propyl]-4-(2-alkyl)-semicarbazide.

17. A compound according to claim 14 wherein said compound is 2-[3-(4-[3-alkoxyphenyl]-1-piperazinyl)propyl]-4-(2-alkyl)-semicarbazide.

* * * * *

UNITED STATES PATENT AND TRADEMARK OFFICE

CERTIFICATE OF CORRECTION

PATENT NO.    : 5,900,485
DATED         : May 4, 1999
INVENTOR(S)   : LEI et al

It is certified that error appears in the above-identified patent and that said letters patent is hereby corrected as shown below:

On the title page:
    item [54], change, "NEOFAZODONE" to --NEFAZODONE--.

Signed and Sealed this

Twenty-ninth Day of May, 2001

Attest:

NICHOLAS P. GODICI

*Attesting Officer*   *Acting Director of the United States Patent and Trademark Office*